United States Patent [19]

Frosch

[11] Patent Number: 4,622,220
[45] Date of Patent: Nov. 11, 1986

[54] PREPARATION FOR ORAL HYGIENE

[75] Inventor: Franz Frosch, Taunusstein, Fed. Rep. of Germany

[73] Assignee: Blendax-Werke R. Schneider, Mainz, Fed. Rep. of Germany

[21] Appl. No.: 702,582

[22] Filed: Feb. 19, 1985

[30] Foreign Application Priority Data

Feb. 20, 1984 [DE] Fed. Rep. of Germany ....... 3406005
Sep. 5, 1984 [DE] Fed. Rep. of Germany ....... 3432571

[51] Int. Cl.$^4$ .............................................. A61K 7/16
[52] U.S. Cl. ...................... 424/49; 424/48; 424/140; 424/145
[58] Field of Search .................. 424/48-58, 424/140, 145

[56] References Cited

U.S. PATENT DOCUMENTS

| | | | |
|---|---|---|---|
| 4,022,880 | 5/1977 | Vinson et al. | 424/50 |
| 4,146,607 | 3/1979 | Ritchey | 424/54 |
| 4,255,419 | 3/1981 | Leopold | 424/145 |
| 4,289,755 | 9/1981 | Dhabbar | 424/52 |
| 4,325,939 | 4/1982 | Shah | 424/55 |
| 4,332,791 | 6/1982 | Raaf et al. | 424/52 |
| 4,339,429 | 7/1982 | Raaf et al. | 424/52 |
| 4,503,070 | 3/1985 | Eby | 514/494 |

FOREIGN PATENT DOCUMENTS

| | | |
|---|---|---|
| 0006708 | 1/1980 | European Pat. Off. . |
| 0011663 | 6/1980 | European Pat. Off. . |
| 0049830 | 10/1980 | European Pat. Off. . |
| 0074082 | 3/1983 | European Pat. Off. . |
| 2052978 | 2/1981 | United Kingdom . |

OTHER PUBLICATIONS

Kietzman C. A. 101 #190152A, (1984), of DTW 91(7/8): 273-6(1984) Oral Substitution of Zinc Deficit with Zinc Aspartate and Zinc Carbonate in Rats.
Hanke, Milton Theo., "Studies on the Local Factors in Dental Caries. I. Destruction of Plaques and Retardation of Bacterial Growth in the Oral Cavity", J. Amer. Den. Assn., vol. 27, No. (1940), pp. 1379-1393.
AADR Abstracts 1975, p. 117.
Literature Reference, vol. 59 (DI), p. 1827.
Afseth, John, "Some Aspects of the Hynamics of Cu and Zn Retained in Plaque as Related to Their Effect on Plaque pH", Scand J. Dent Res. 1983, vol. 91, pp. 169-174.
Afseth, John, "Accumulation of Cu and Zn in Human Dental Plaque in Vivo", Caries Res. 17:310-314, (1983).
Saxer, U. P. et al, "Synergistic Antiplaque Effects of a Zinc Fluoride/Hexetidine Containing Mouthwash. A Review", HOA vol. 27; 1-16; Aug. 1983.
Afseth, John et al, "Effect of Copper Applied Topically or in Drinking Water on Experimental Caries in Rats", Caries Res. 18:434-39, (1984).

*Primary Examiner*—Shep K. Rose
*Attorney, Agent, or Firm*—Birch, Stewart, Kolasch & Birch

[57] ABSTRACT

A composition for oral hygiene with improved efficacy against dental plaque, said composition containing zinc aspartate and/or copper aspartate, preferably in an amount of 0.05 to 5% by weight based on the total weight of the composition.

9 Claims, No Drawings

PREPARATION FOR ORAL HYGIENE

The present invention is related to a preparation for oral hygiene, especially a tooth and mouth care agent with an activity against dental plaque formation containing zinc aspartate and/or copper aspartate as active ingredients.

The use of zinc compounds in oral hygiene agents, especially to prevent or decrease the formation of dental plaque, has been well-known for a long time, e.g., as disclosed in Dutch Patent Application No. 7,102,432.

In this publication zinc citrate is the preferred zinc salt. The use of zinc citrate in combination with alkali salts and the application of ammonium or alkali zinc citrate in tooth and mouth care agents have been already described in U.S. Pat. Nos. 4,289,755 and 4,325,939 as well as German Offenlegungsschrift No. 3,021,150. By using that complex salts the solubility of the slightly water-soluble zinc citrate is increased.

There is also a toothpaste on the market containing zinc citrate as the active ingredient. However, as shown by clinical testing, a significant plaque-reducing effect of zinc citrate could not be investigated in a double-blind study, see IADR Abstracts of the British Division No. 145, Journal of Dental Research, Vol. 59/Special Issue D/Part I (1981), p. 1827.

It was also proposed to use other zinc compounds such as zinc salicylate, zinc lactate, zinc gluconate (Published European Patent Application No. 74,082), complex zinc compounds with carboxymethyl oxysuccinic acid (Published European Patent Application No. 67,08) and especially zinc acetate (Journal of the American Dental Association, Vol. 27/No. 9 (1940), p. 1379-1393).

To overcome the above referred to disadvantages and to improve the efficacy against dental plaque, it was suggested to use zinc salts in admixture with different active ingredients known to prevent plaque formation to reach a synergistic effect. In this respect, attention should be drawn to the combination of zinc salts, especially zinc fluoride, and hexetidine disclosed in Schweizerische Monatsschrift für Zahnheilkunde, Vol. 93 (1983), p. 689-704, and Published European Patent Application No. 49,830.

In addition, a synergistic effect was alleged for a combination of tetradecyl amine and zinc salts in U.S. Pat. No. 4,146,607 and European Pat. No. 11,663.

Finally, Published British Patent Specification No. 2,052,978 discloses the combination of zinc compounds with glycine.

However, in spite of all these various methods and combinations it was not possible in practice to prepare agents for oral hygiene containing zinc compounds which are stable and which show sufficient efficacy against dental plaque, although the principal usefulness of zinc compounds for that purpose is generally acknowledged as may be shown from several scientific articles published in Caries Research, Vol. 17 (1983), p. 310-314, Scandinavian Journal of Dental Research, Vol. 9 (1983), p. 169-174, and particularly a dissertation of J. Afseth (Oslo, 1983).

It has been found and is an object of the present invention, that stable compositions for oral hygiene which are very efficient against dental plaque containing zinc compounds may be prepared when zinc aspartate is used as zinc compound. The zinc aspartate may be applied as the only zinc compound or in admixture with other zinc ions releasing components. However, in any case it is suitable that zinc aspartate is present in an amount of more than 50% by weight of a possible mixture of zinc compounds.

It is further known that the copper cations prevent formation of dental plaque when topically applied from solutions of copper compounds onto teeth surfaces (AADR Abstracts 1979, No. 117; Caries Research, Vol. 18 (1984), p. 434-439).

Copper ion releasing compounds do not show the disadvantages which are well-known in other plaque-preventing compounds, such as antimicrobial quaternary ammonium compounds or chlorhexidine salts, i.e., the staining of the teeth and tongue after long-term application.

However, the use of copper ion releasing components in toothpastes containing additional carrier materials and active and inactive ingredients could not be effected as they were inactivated by several of those ingredients or they did not keep their activity at the required pH-value.

In European Pat. Nos. 38,867 and 38,868 toothpaste compositions are described containing copper compounds in active condition. This is achieved by an optimal selection of the corresponding polishing agents.

Although those compositions have been shown to be generally active against dental plaque, it is desirable not to be limited in the selection of polishing agents and the pH-value, to certain components or ranges.

So the problem to be solved is to develop a tooth and mouth care composition with plaque-preventing activity releasing copper ions which is not limited to special components, and whose activity is not diminished or inhibited by compounds usually present in such compositions.

It has been found that the solution the this problem is to use, as the active ingredient for releasing copper ions, the copper salt of aspartic acid, i.e., copper aspartate.

Copper aspartate is compatible with nearly all polishing agents and other ingredients commonly used in tooth and mouth care agents. Moreover, it may be applied and remains active over a broad pH-range between about 4 and about 10.

Copper aspartate and zinc aspartate may be added to the compositions according to the present invention as such; however, it is also possible to prepare them in the composition itself in situ by reaction of aspartic acid with soluble copper or zinc compounds such as copper sulphate, copper chloride, zinc sulphate, etc.

The preferred percentage of copper aspartate and zinc aspartate is between about 0.05 and about 5% by weight of the total composition, especially between about 0.25 and about 2.5% by weight.

From the following animal tests described hereunder the superior efficacy of zinc aspartate on one hand as well as copper aspartate on the other hand is shown in comparison with toothpastes containing zinc citrate, zinc acetate, a "synergistic mixture" containing zinc citrate and hexetidine, or copper sulphate, and untreated control groups.

TEST REPORT A 20 days old Osborne-Mendel rats were divided into 5 groups with 16 animals each, with each group receiving the plaque standard diet 2000 S. At the beginning of the test from each test animal the initial plaque status was investigated. Then the animals were inoculated with 0.1 ml of a standardized bacterial suspension of ACTINO- MYCES viscosus OMZ 105. Further inoculations were carried out each week.

The treatment of the test animals with the preparations to be investigated begins at the 23rd life day. Twice daily 0.1 ml test preparation/test animal are applied by a syringe. After 5 weeks the animals were sacrificed and the plaque formation was investigated on the 2 first buccal surfaces and the first 4 lingual surfaces of the molars 1 and 2 in the upper jaw; i.e., 12 surfaces total per animal.

The evaluation is carried out after coloration with erythrosin solution according to the following scheme:
0: no plaque.
1: up to ⅓ of the surface is covered with plaque.
2: up to ⅔ of the surface are covered with plaque.
3: more than ⅔ of the surface are covered with plaque.

The corresponding points are summed up and the average value is calculated.

| Group | Result Sx | $\bar{x}$ | $\sigma$ |
|---|---|---|---|
| 1 | 227 | 14,19 | 4,56 |
| 2 | 256 | 16,00 | 4,72 |
| 3 | 165 | 10,31 | 3,28 |
| 4 | 249 | 15,56 | 4,03 |
| 5 | 342 | 21,38 | 2,70 |

EXAMPLE A

α-Alumina trihydrate: 58.5 (% by weight)
Sorbitol solution (70%): 25.5
Xanthan gum: 0.6
Sodium monofluorophosphate: 0.8
Saccharin sodium: 0.1
Preservative: 0.3
Sodium lauryl sulphate: 0.4
Flavour mixture: 0.1
Zinc aspartate: 0.5
Water: ad 100.0

COMPOSITION OF TOOTHPASTES

Group 1: According to Example A, however, zinc aspartate was substituted by 0.05% hexetidine and 0.5% zinc citrate.2H$_2$O (=0.16% Zn).
Group 2: According to Example A, however, zinc aspartate was substituted by 0.5% zinc citrate.2H$_2$O (=0.16% Zn).
Group 3: Toothpaste according to Example A.
Group 4: According to Example A, however, zinc aspartate was substituted by 0.55% zinc acetate.2H$_2$O (=0.16% Zn).
Group 5: Untreated control group.

The equivalence of weight to 100% was effected by variation of the water percentage.

The result shows the surprising superiority of zinc aspartate, even against a mixture defined as "synergistic mixture" in the prior art containing zinc compounds and hexetidine.

TEST REPORT B

The methods were the same as described in test report A.

| Group | Result $\bar{x}$ |
|---|---|
| 1 | 10,31 +/− 3,42 |
| 2 | 10,75 +/− 3,26 |
| 3 | 8,44 +/− 2,06 |
| 4 | 20,50 +/− 3,32 |
| 5 | 23,94 +/− 2,43 |

EXAMPLE A

α-Alumina trihydrate (particle size about 1–15 μm): 58.50% (by weight)
Sorbitol solution (70%): 25.50
Xanthun gum: 0.60
Sodium monofluorophosphate: 0.80
Saccharin sodium: 0.10
Preservative: 0.30
Sodium lauryl sulphate: 0.40
Flavour mixture: 0.10
Copper aspartate: 0.26
Water: ad 100.00

EXAMPLE B

Synthetic zeolite A (Na$_{12}$(AlO$_2$)$_{12}$(SiO$_2$)$_{12}$.27H$_2$O): 24.00% by weight
Dicalcium orthophosphate: 10.00
Carboxymethyl cellulose: 1.20
Sodium lauryl sulphate: 2.00
Glycerol: 6.00
Sorbitol: 15.00
Preservative: 0.30
Flavour mixture: 1.00
Colloidal silica: 1.55
Saccharin sodium: 0.05
Sodium monofluorophosphate: 0.80
Copper aspartate: 0.25
Water: ad 100.00

EXAMPLE C

Calcium carbonate: 41.00% by weight
Sodium lauryl sulphate: 1.50
Hydroxymethyl cellulose: 1.30
Sorbitol: 9.00
Sodium monofluorophosphate: 0.80
Flavour mixture: 1.00
Saccharin sodium: 0.10
Preservative: 0.25
Copper aspartate: 0.25
Water: ad 100.00

COMPOSITION OF TOOTHPASTES

Group 1: According to Example A.
Group 2: According to Example B.
Group 3: According to Example C.
Group 4: According to Example C, except copper aspartate was substituted by 0.20% copper sulphate (=0.05% Cu).
Group 5: Untreated control group.

The weight equivalence to 100% in group 4 was effected by variation of the water percentage.

The results show the surprising superiority of copper aspartate to a composition containing copper sulphate in identical Cu concentration, even in the alkaline pH-range.

The compositions for oral hygiene according to the invention may be applied in various application forms. Toothpastes, either opaque or transparent, mouthwashes and chewing gum are preferred. However, any different application form like mouth spray, sucking or chewing tablets, or tooth powders are suitable carrier materials.

As mentioned, the toothpaste may be opaque or transparent. Transparent toothpastes contain polishing agents having the same refraction index as the carrier material.

Especially suitable polishing agents are alumina, especially as trihydrate, such as α-alumina trihydrate, having a preferred particle size between about 1 and about 20, especially about 10 μm, and calcium carbonate.

Of course, it is also possible to prepare toothpastes based on other carrier materials, containing as polishing agents e.g. alkali aluminum silicates, e.g. zeolites A as disclosed in the European Patent Specification Nos. 2,690 and 3,023, different calcium phosphates like dicalcium orthophosphate as dihydrate or water-free, tricalcium phosphate, calcium pyrophosphate, insoluble alkali metaphosphate, silicas of different modifications, such as silica-xerogels, -hydrogels or precipitated silicas, or powdered plastic materials like polymethyl methacrylate with a particle size distribution between about 0.5 and about 5 μm.

Of course, also mixtures of suitable polishing agents may be applied, e.g., a mixture of α-alumina hydrate and/or calcium carbonate and synthetic zeolite A in a ratio of about 1:1.

The total polishing agent percentage in the toothpastes according to the invention is preferably between about 20 and about 60% by weight of the total composition.

The usual surface-active agents may be used in an amount up to about 2.5% by weight of the total composition of the oral hygiene agents.

Suitable synthetic surface-active agents are, e.g., alkyl sulphates, alkyl ether sulphates, olefine sulphonates, sodium lauroyl sarcosinate, or ampholytic, nonionic or cationic compounds or soaps like alkali salts from lauric acid, myristic acid, palmitic acid, stearic acid or mixtures thereof, e.g. coconut oil fatty acid or tallow fatty acid.

A review of suitable compositions for toothpastes and their preparation is given in the monography of M. S. Balsam/E. Sagarin, "Cosmetics-Science and Technology", 2nd Ed., Vol. 1, p. 423–533 (1972), the disclosure of which is included by reference.

Toothpastes normally contain moisturizers in an amount between about 10 and about 35% by weight. Suitable moisturizers are glycerol, diols like 1,4-butanediol or 1,2-propanediol or sugar alcohols like sorbitol, mannitol or xylitol and also polyethylene glycols with low molecular weights.

Also contained in toothpastes are thickening agents, whose amount in toothpastes is between about 0.25 and about 5% by weight of the total composition.

Suitable thickening agents are carboxymethyl cellulose and its alkali salts, especially sodium carboxymethyl cellulose, hydroxyalkyl celluloses like hydroxymethyl cellulose and hydroxyethyl cellulose, methyl cellulose, natural gums like tragant, Gum arabicum, caraya gum, guar gum, xanthan gum and Irish moss, synthetic polyelectrolytes like alkali salts of polyacrylic acid as well as inorganic thickening compounds, especially colloidal magnesium aluminium silicate or silica.

The compositions for oral hygiene according to the invention of course may contain additional active ingredients. Especially the incorporation of the well-known carriers such as prophylactic fluorides is advantageous, preferably in such an amount that the concentration of pure F in the composition is between about 0.05 to about 1% F by weight, particularly between 0.1 to 0.5% by weight of the total composition.

Suitable fluorine components are the different salts of the monofluorophosphoric acid such as sodium, potassium, lithium, calcium, and aluminum mono- and difluorophosphate as well as the various ionic fluorides, particularly alkali fluorides like sodium, lithium, potassium, and ammonium fluoride, stannous fluoride, manganese fluoride, copper fluoride, zirconium fluoride, aluminum fluoride as well as mixtures or adducts of these fluorides, e.g., alkali manganese fluorides.

The oral hygiene agents according to the present invention may additionally contain further ingredients like other plaque-inhibiting substances, ingredients preventing the formation of dental calculus such as hydroxy ethane-1,1-diphosphonic acid or alkylene amino tetramethylene phosphonic acids and their water-soluble salts, allantoin, azulene, etc.

The following examples should characterize the principle of the invention:

| Component | Toothpastes Example No. | | | | | | | |
|---|---|---|---|---|---|---|---|---|
| | 1 | 2 | 3 | 4 | 5 | 6 | 7 | 8 |
| α-Aluminum hydroxide (% by weight) | 35,0–60,0 | | | | 35,0–60,0 | | | |
| Colloidal silica | 0,5–4,0 | 0,5–4,0 | 0,5–4,0 | 0,5–2,0 | 0,5–4,0 | 0,5–4,0 | 0,5–4,0 | 0,5–4,0 |
| Sodium lauryl sulphate | 1,0–2,0 | 1,0–2,0 | 1,0–2,0 | 1,0–2,0 | 1,0–2,0 | 1,0–2,0 | 1,0–2,0 | 1,0–2,0 |
| Sorbitol | 5,0–30,0 | 5,0–80,0 | 5,0–30,0 | 5,0–30,0 | 5,0–30,0 | 5,0–80,0 | 5,0–30,0 | 5,0–30,0 |
| Glycerol | 5,0–30,0 | 5,0–30,0 | 5,0–30,0 | 5,0–30,0 | 5,0–30,0 | 5,0–30,0 | 5,0–30,0 | 5,0–30,0 |
| Binding agent (xanthum gum, carboxymethyl cellulose) | 0,5–2,0 | 0,5–2,0 | 0,5–2,0 | 0,5–2,0 | 0,5–2,0 | 0,5–2,0 | 0,5–2,0 | 0,5–2,0 |
| Preservative | 0,1–0,3 | 0,1–0,3 | 0,1–0,3 | 0,1–0,3 | 0,1–0,3 | 0,1–0,3 | 0,1–0,3 | 0,1–0,3 |
| Saccharin sodium or Sodium cyclamate | 0,1–0,3 | 0,1–0,3 | 0,1–0,3 | 0,1–0,3 | 0,1–0,3 | 0,1–0,3 | 0,1–0,3 | 0,1–0,3 |
| Flavour mixture | 0,8–1,5 | 0,8–1,5 | 0,8–1,5 | 0,8–1,5 | 0,8–1,5 | 0,8–1,5 | 0,8–1,5 | 0,8–1,5 |
| Sodium monofluorophosphate | 0,5–1,2 | 0,5–1,2 | 0,5–1,2 | 0,5–1,2 | 0,5–1,2 | 0,5–1,2 | 0,5–1,2 | 0,5–1,2 |
| Sodium fluoride | 0,05–0,2 | 0,05–0,2 | — | 0,05–0,2 | 0,05–0,2 | 0,05–0,2 | — | 0,05–0,2 |
| Zinc aspartate | 0,25–2,5 | 0,25–2,5 | 0,25–2,5 | 0,25–2,5 | 0,25–2,5 | 0,25–2,5 | 0,25–2,5 | 0,25–2,5 |
| Silica-Xerogel (2–15 μm; 700 m²/g) | 15,0–25,0 | | | | | 15,0–25,0 | | |
| Precipitated calcium carbonate | | | 30,0–50,0 | | | 30,0–50,0 | | |
| Polymethyl methacrylate powder | | | | 35,0–55,0 | | | | 35,0–55,0 |
| Water | ad 100,0 | ad 100,0 | ad 100,0 | ad 100,0 | ad 100,0 | ad 100,0 | ad 100,0 | ad 100,0 |

EXAMPLE 9

Mouthwash concentrate

Flavour mixture: 5.00 (% by weight)
Zinc aspartate: 3.30
Zinc citrate.$2H_2O$: 0.25
Nonionic emulsifier: 1.80
n-Propanol: 5.00
1-Methoxypropanol: 35.00
Glycerol: 8.50
Phenyl salicylate: 0.55
Saccharin sodium: 0.30
Water: 40.30

Before use, the concentrate is diluted with water in a ratio of 1:4.

EXAMPLE 10

Chewing gum

Gum base: 30.00
Sorbitol: 25.00
Xylitol: 20.00
Saccharin sodium: 0.30
Zinc acetate.$2H_2O$: 0.30
Zinc aspartate: 2.40
Copper sulphate.$2H_2O$: 0.30
Glycerol: 2.00
Flavour mixture: 3.70
Ascorbic acid: 1.00
Fructose: 15.00

EXAMPLE 11

Mouthwash concentrate

Flavour mixture: 5.00 (% by weight)
Copper aspartate: 2.50
Zinc citrate.$2H_2O$: 0.25
Nonionic emulsifier: 1.80
n-Propanol: 5.00
1-Methoxypropanol(-2): 35.00
Glycerol: 8.50
Phenyl salicylate: 0.55
Saccharin sodium: 0.30
Water: ad 100.00

The concentrate is diluted with water in a ratio of 1:4 before use.

EXAMPLE 12

Chewing gum

Gum base: 30.00
Sorbitol: 25.00
Xylitol: 20.00
Saccharin sodium: 0.30
Copper fluoride: 0.50
Copper aspartate: 2.20
Copper sulphate.$2H_2O$: 0.30
Glycerol: 2.00
Flavour mixture: 3.70
Ascorbic acid: 1.00
Fructose: 15.00

We claim:

1. A toothpaste composition effective against the formation of dental plaque containing from 0.05 to 5% by weight, based on the total weight of the composition, of a member selected from the group consisting of zinc aspartate, copper aspartate and mixtures thereof.

2. The composition of claim 1, wherein the zinc aspartate or copper aspartate is present in an amount of 0.25 to 2.5% by weight, based on the total weight of the composition.

3. A toothpaste composition according to claim 1, containing zinc aspartate and a polishing agent which is composed of more than 50% alumina hydrate.

4. A toothpaste composition according to claim 1, containing copper aspartate and a polishing agent which is composed of more than 50% of calcium carbonate.

5. A method for preventing the formation of dental plaque which comprises treating the teeth with a toothpaste composition in accordance with claim 1.

6. Aqueous toothpaste composition according to claim 1, containing copper aspartate and a polishing agent being composed to more than 50% of calcium carbonate.

7. Aqueous toothpaste composition according to claim 1, containing copper aspartate and a polishing agent being composed to more than 50% of calcium carbonate.

8. The method of claim 5 wherein the zinc aspartate or copper aspartate is present in amount of 0.25 to 2.5% by weight based on the total weight of the composition.

9. The method of claim 5 wherein the composition is an aqueous toothpaste composition.

* * * * *